United States Patent [19]

Strong

[11] Patent Number: 4,662,211

[45] Date of Patent: May 5, 1987

[54] MEASURING FRICTION CHARACTERISTICS OF VEHICLE TRAVEL SURFACES

[75] Inventor: James W. Strong, Berkley, Mich.

[73] Assignee: K. J. Law Engineers, Inc., Farmington Hills, Mich.

[21] Appl. No.: 809,299

[22] Filed: Dec. 16, 1985

[51] Int. Cl.$^4$ ............................................ G01N 19/02
[52] U.S. Cl. ........................................................ 73/9
[58] Field of Search ...................... 73/9, 129, 128, 146; 364/424

[56] References Cited

U.S. PATENT DOCUMENTS

| | | | |
|---|---|---|---|
| 3,893,330 | 7/1975 | Shute et al. | 73/9 |
| 3,948,080 | 4/1976 | Boyd | 73/9 |
| 4,098,111 | 7/1978 | Hardmark et al. | 73/9 |
| 4,212,063 | 7/1980 | Hardmark | 73/9 |

FOREIGN PATENT DOCUMENTS 2292971  6/1976  France ....................... 73/9

Primary Examiner—Stewart J. Levy
Assistant Examiner—Robert R. Raevis
Attorney, Agent, or Firm—Barnes, Kisselle, Raisch, Choate, Whittemore & Hulbert

[57] ABSTRACT

Apparatus for measuring friction characteristics of a vehicle-travelled surface comprising a wheeled vehicle having a test wheel assembly pivotally suspended therefrom by a parallelogram suspension arrangement. The test wheel assembly includes a test wheel carried by a drive shaft which is driven at predetermined slip by a differential coupled to the vehicle wheels. A gear chain extends from the differential to the drive shaft through a housing which forms one arm of the suspension. The second arm is formed by a rod which extends from the differential to one section of a two-axis strain gage wheel force transducer at the test wheel assembly. The differential is suspended by parallel struts from the vehicle frame. A positive displacement pump is coupled to the differential for placing a film of water beneath the test wheel having a thickness which is independent of vehicle speed. The pump and test wheel are clutch driven.

16 Claims, 7 Drawing Figures

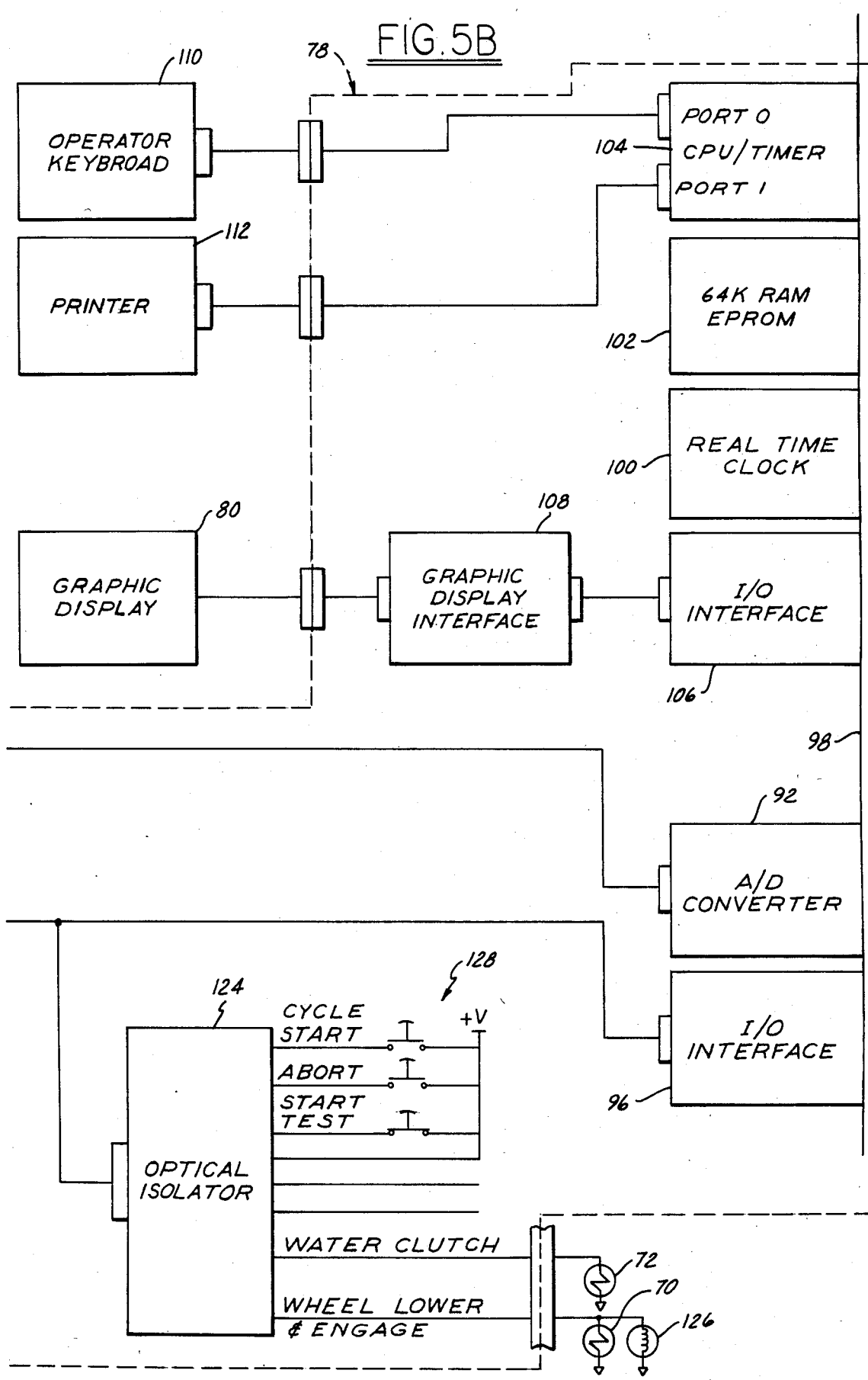

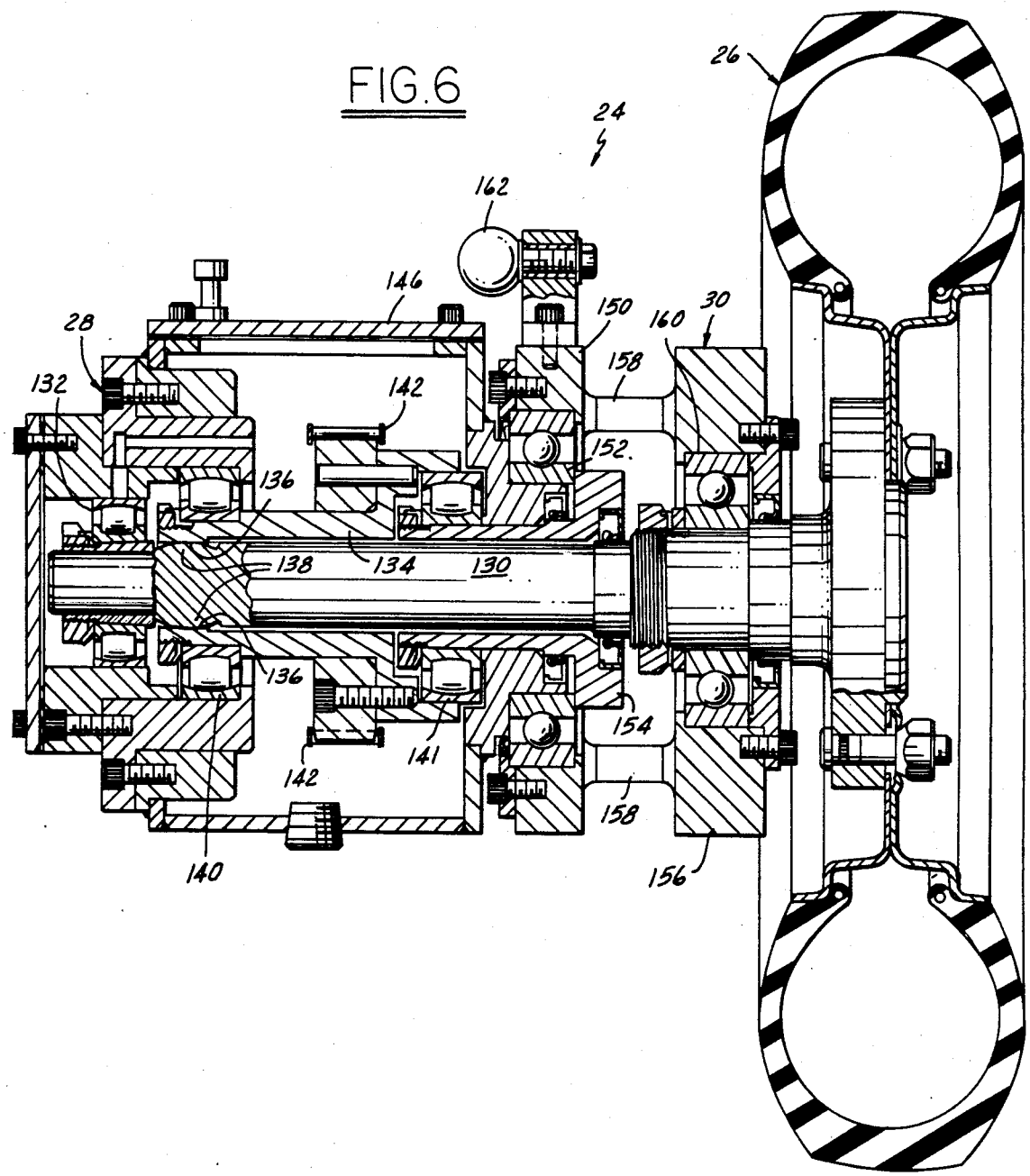

MEASURING FRICTION CHARACTERISTICS OF VEHICLE TRAVEL SURFACES

The present invention relates to apparatus for measuring friction characteristics of a vehicle-travelled surface, such as coefficient of incipient slip force friction of an airport runway or automobile highway.

BACKGROUND OF THE INVENTION

Desirability of measuring friction characteristics of vehicle-travelled surfaces, particularly airport runways, has long been recognized in the art, and a number of apparatus have been developed to fulfill this need. In general, apparatus of this type include a test wheel mounted on a vehicle which is adapted to be propelled over the test surface. In some devices, the test wheel is mounted at an angle to the direction of travel, and surface friction characteristics are measured as a function of forces which tend to align the test wheel with the vehicle direction. In other devices, the test wheel rotates in the direction of travel, and angular velocity of the test wheel is retarded with respect to the vehicle wheels, either at a predetermined fixed "slip" ratio, or at an increasing ratio to wheel skid and lock-up. Surface friction characteristics are measured as a function of forces acting on the test wheel, such as horizontal or braking force, vertical force or load, and brake torque.

French Pat. No. 1,015,251 (1952) discloses an early apparatus in which a test wheel on a self-propelled vehicle is carried on a pivot arm which is selectively lowered by an electric winch into engagement with the test surface at an angle to the direction of vehicle travel. Transducers measure forces on the wheel for determining surface friction characteristics. French Pat. No. 1,476,730 (1967) discloses a similar apparatus wherein test wheels are mounted on respective pivot arms, again on a self-propelled vehicle. The pivot arms and test wheels are coupled to an hydraulic system for selectively lowering the wheels against the test surface and applying a constant vertical load thereto. One wheel is oriented in the direction of travel and may be braked to obtain a predetermined slip with respect to the remaining vehicle wheels. A nozzle directs a film of water beneath the test wheels for simulating wet pavement conditions.

Kullberg, "Method and Equipment for Continuous Measuring of the Coefficient of Friction at Incipient Skid," NAS Highway Research Board Bulletin 348 (1962), pages 18-35, describes a number of early test vehicles constructed by the National Swedish Road Research Institute in Stockholm, Sweden. In general, the various vehicles are self-propelled and employ belt transmissions coupled at variable gear ratio to the vehicle drive system for obtaining fully controlled slip at the test wheels. The test wheels can be raised and lowered selectively by the operator. Vertical wheel load and either horizontal force or wheel torque are measured to obtain friction characteristics, including specifically coefficient of friction, by dividing horizontal force by vertical wheel load. A tachometer on the test wheel indicates test wheel speed. A pump and nozzle place a film of water beneath the test wheel. A number of the vehicles also include facility for programmable control of test distances.

Kummer et al, "Measurement of Skid Resistance," Symposium on Skid Resistance, Special Technical Pub. No. 326, ASTM (1962) and "The Penn State Road Friction Tester as Adapted to Routine Measurement of Pavement Skid Resistance," Hwg. Res. Record No. 28, NAS Hwy. Res. Bd. (1963) contain a general discussion of coefficient of friction and measurement thereof, as well as a specific device for performing such measurement. A test wheel is mounted behind a vehicle as a fifth wheel by a parallel strut arrangement. A drum brake provides selective braking of the test wheel, with the brake backing plate being restrained by a control link of the parallelogram suspension. A force transducer in the control link measures traction force. An air cylinder selectively raises and lowers the test wheel assembly, and a pump places a water film beneath the test wheel.

FAA Report No. ADS-55, "Design and Development of an Airport Runway Surface Traction Measuring Device," (1966) describes a test vehicle which includes, among other features, a positive displacement pump coupled to the vehicle drive system for maintaining uniform water film thickness beneath the test wheel independently of vehicle speed. An hydraulic transmission is employed to obtain controlled slip at a trailer-mounted test wheel. Domandl, "Measuring Tire Friction Under Slip with the Penn State Road Friction Tester," NAS Hwy. Res. Bd., Hwy. Res. Rec. No. 214 (1968), pages 34-41 also discloses test apparatus which embodies hydraulic control to obtain predetermined slip at the test wheel. Strain gages are employed for measuring forces on the parallelogram-suspended test wheel, and coefficient of friction and friction number are both indicated. Devices heretofore marketed in the U.S. under the trade designations "Skidometer BV6" and "Skidometer BV11:2" (1971) embody many principles attributed to Kullberg, including controlled slip at the test wheel and strain gages for measuring forces acting thereon. In addition, the BV11:2 apparatus featured operator switch selection of runways by number and preprogrammed runway test lengths.

Rizenbergs et al, "Skid-Test Trailer: Description, Evaluation and Adaptation," Kentucky Dept. of Hwys., Report No. 338 (1972) describes construction and evaluation of a two-wheeled test trailer heretofore marketed by applicant's assignee under the designation "Model 965A Pavement Friction Tester." Each wheel of the test trailer is coupled to a disc brake selectively powered by an hydraulic pump carried by the tow vehicle for braking the test wheels with respect to vehicle velocity. Pumps are coupled through electric clutches and gear belts to the vehicle drive shaft for applying uniform water films beneath each trailer wheel independently of vehicle speed. A four-beam two-axis strain gage force transducer is coupled to each test wheel for indicating instantaneous wheel load and traction force. The strain gages are connected in a bridge arrangement such that the horizontal and vertical forces are additive. Boyd U.S. Pat. No. 3,948,080 discloses a tire traction tester which employs a three-axis "Model 2500" version of the same transducer.

The foregoing prior art is epitomized in the disclosures of U.S. Pat. Nos. 4,098,111 and 4,212,063.

OBJECTS AND SUMMARY OF THE INVENTION

It is a general object of the present invention to provide apparatus for measuring friction characteristics of a vehicle travel surface which obtains improved economy, operating efficiency and accuracy, while at the same time reducing causes of wear and failure of moving parts.

It is a more specific object of the invention to provide measurement apparatus of the described character which obtains improved accuracy by maintaining desired orientation of force measurement transducers at the test wheel regardless of irregularities and undulations in the test surface.

These and other objectives are implemented in apparatus which includes a wheeled vehicle constructed to be propelled along a test surface in a predetermined direction. A test wheel assembly includes a test wheel carried by a hub to rotate about an axis perpendicular to the direction of vehicle travel, with transducers being mounted on the hub and coupled to the test wheel for dynamically measuring forces acting on the test wheel horizontally in the direction of travel and vertically perpendicular to the direction of travel. A drive mechanism is coupled to at least one wheel of the vehicle and to the test wheel for driving the test wheel at predetermined slip with respect to the vehicle wheel. In accordance with an important feature of the invention, the drive mechanism is suspended from the vehicle frame against rotation about the axis of the vehicle wheel coupled thereto, and the test wheel transducer is suspended from the drive mechanism against rotation with respect to the test wheel axis. In this way, transducer orientation is maintained independently of undulations in the test surface.

In the specific preferred embodiment of the invention herein disclosed, the test wheel drive mechanism includes a differential coupled to opposed vehicle wheels and a gear drive extending from the differential to the test wheel assembly. At the test wheel assembly, a wheel drive shaft is rotatably mounted at one end within the hub and is coupled by a crowned spline arrangement to the gear drive for maintaining a lever arm of substantially constant length from the drive to the transducer. The transducer includes a first section rotatably mounted to the hub and coupled to the suspension against rotation about the drive shaft. A second transducer section rotatably supports the drive shaft. The transducer sections are coupled by strain gages for indicating forces on the test wheel as a function of tilting of the wheel drive shaft.

Further specific features of the preferred embodiment are embodied include an electric winch carried by the vehicle frame provides for selective raising and lowering of the test wheel assembly. An electric clutch at the test wheel drive provides for selective connection of the test wheel to the differential for reducing stresses upon initial engagement of the test wheel with the road surface. A positive displacement water pump is coupled to the differential by a second gear drive and a second electric clutch for feeding water from a tank to a nozzle, and thereby obtaining a film of water beneath the test wheel having a thickness which is independent of vehicle speed. Equipment electronics within the vehicle cab are responsive to the test wheel force transducers and to an operator keyboard for automatically reading and recording test data and displaying the same to the vehicle operator.

BRIEF DESCRIPTION OF THE DRAWINGS

The invention, together with additional objects, features and advantages thereof, will be best understood from the following description, the appended claims and the accompanying drawings in which:

FIGS. 5A and 5B together comprise a semi-schematic and semi-functional block diagram of measurement and display electronics in accordance with the preferred embodiment of the invention; and FIG. 6 is a sectional view taken substantially along the line 6—6 in FIG. 3.

DETAILED DESCRIPTION

Figure 1:
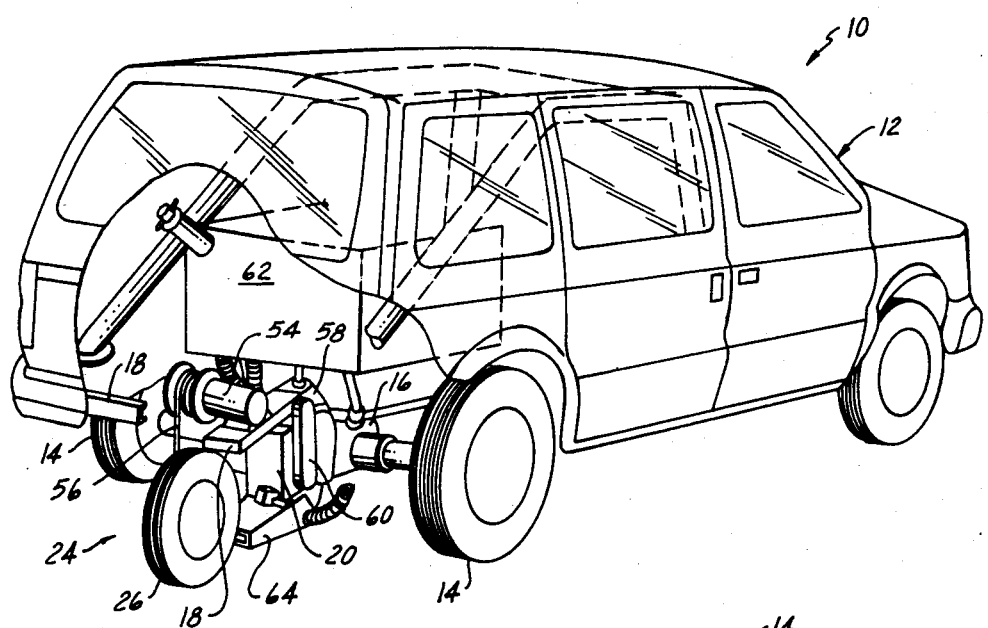
FIG. 1 is a rear perspective view of a vehicle equipped with test apparatus in accordance with the invention.
Figure 2:
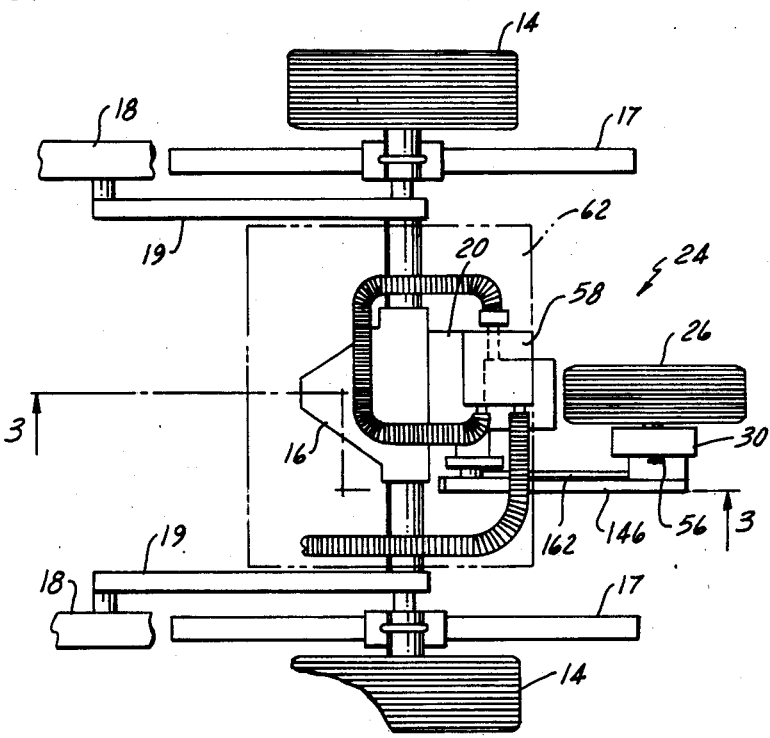
FIG. 2 is a fragmentary plan view of the test apparatus illustrated in FIG. 1.

FIGS. 1–3 and 6 illustrate a presently preferred embodiment of test apparatus 10 in accordance with the invention as comprising a self-propelled front-wheel drive vehicle 12 having rear wheels 14 coupled to a conventional differential 16. Vehicle 12 has a frame generally indicated at 18 with wheels 14 and differential 16 being suspended therefrom by the floating leaf springs 17 and by the parallel struts 19. Struts 19 are of equal length, and are each pivotally coupled at one end to frame 18 and at opposing ends to the axle housings of wheels 14 and thus to differential 16. Thus, struts 19 restrain differential 16 from rotation with respect to frame 18 about the axis of wheels 14 in the event of vertical displacement of wheels 14 due to undulations in the test surface 32. A power take-off 20 is mounted on differential 16 and provides rotary output at a shaft 22 at predetermined angular velocity with respect to angular velocity of vehicle wheels 14. A test wheel assembly 24 includes a test wheel 26 carried by a hub 28 (FIG. 6) for rotation about a wheel axis which is substantially fixed with respect to hub 28. A conventional two-axis strain gage force transducer 30 is carried by hub 28 for measuring horizontal and vertical forces on test wheel 26, and thereby indicating friction characteristics between test wheel 26 and vehicle-travelled surface 32.

Figure 3:
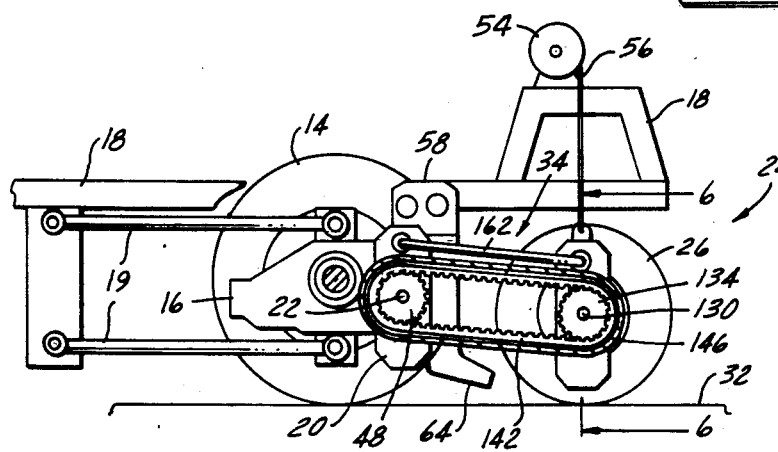
FIG. 3 is a sectional view taken substantially along the line 3—3 in FIG. 2.

Referring in particular to FIG. 6, a test wheel drive shaft 130 is rotatably mounted at one end by the bearing 132 within hub 28. Test wheel 26 is mounted to the opposing end of shaft 130. A collar 134 surrounds shaft 130 and is drivably coupled thereto adjacent to hub bearing 132 by axial internal splines 136 on collar 134 and crowned external splines 138 on shaft 130. Collar 134 is supported within hub 28 by the bearings 140,141. Collar 134 is coupled to a gear 48 (FIG. 3) on shaft 22 by an endless gear chain 142 for thereby driving collar 134, shaft 130 and test wheel 26 at predetermined slip with respect to vehicle wheels 14 (FIG. 3). A housing 146 surrounds and encloses gear chain 142 and is pivotally coupled at one end (by means not shown) to differential power take-off 20 and is affixed at the opposing end to hub 28 (FIG. 6), which is itself pivotal about the axis of shaft 130 by means of bearings 132,140,141.

Transducer 30 includes a first section 150 which surrounds shaft 130 and is axially affixed to hub 28 and housing 146 by the bearing 152 and clamp 154 so as to be rotatable with respect thereto about the axis of shaft 130. A second section 156 of transducer 30 surrounds shaft 130 and carries a bearing 160 which rotatably supports shaft 130 adjacent to test wheel 26 and remotely of drive splines 136,138. Transducer sections 150,156 are fixedly coupled to each other by four strain gage bridges or beams 158. A control arm 162 is pivotally mounted at one end to power take-off 20 (FIG. 3) and at the opposing end to transducer section 150 (FIG. 6) so as to restrain transducer section 150 from rotation. The length of control arm 162 (which may be adjustable) between its pivots is identical to the length between the axes of shafts 22 (FIG. 3) and 130. It will thus be appreciated that housing 146 and control arm 162 form a parallelogram suspension 34 which restrains rotation of transducer 30 about the axis of shaft 130.

Transducer 30, but not mounting thereof as hereinabove described, is essentially identical in structure and function to that disclosed in Rizenbergs et al, above. In general, forces on test wheel 26 tilt shaft 130 and thereby displace transducer sections 150,156 with respect to each other. Such displacement is sensed at strain gage bridges 158. Crowned spline drive arrangement 136,138 helps maintain a substantially constant lever arm from the spline drive to transducer section 156, and helps maintain measurement accuracy. An electric winch 54 (FIGS. 1 and 3) is mounted on frame 18 and has a cable 56 which extends and is coupled to test wheel assembly 24. Winch 54 is thus selectively operable by a vehicle operator for raising and lowering test wheel assembly 24. A positive displacement pump 58 is coupled by a gear chain 60 (FIG. 1) to power take-off 20 and is connected between a water tank 62 and a nozzle 64 for supplying a film of water beneath test wheel 26 of uniform thickness independently of vehicle speed, and thereby simulating wet-weather conditions in testing of the road surface.

Figure 4:
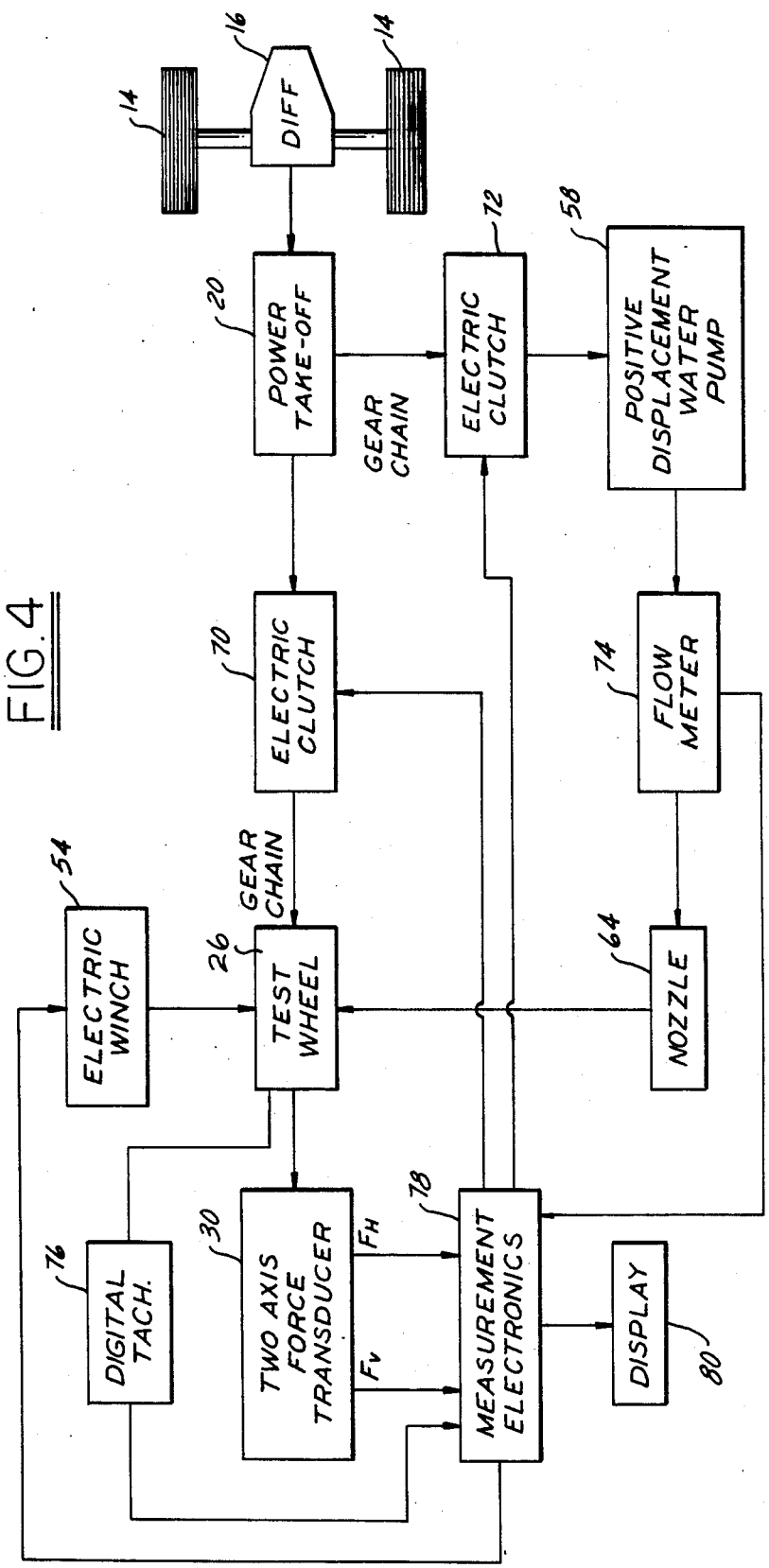
FIG. 4 is a functional block diagram of a presently preferred embodiment of test apparatus in accordance with the invention.

FIG. 4 is a functional block diagram of test apparatus 10. Vehicle wheels 14 are coupled by differential 16 to power take-off 20. Power take-off 20 is connected by gear chain 142 through an electric clutch 70 (not shown in FIGS. 1-3) to test wheel 26. Electric clutch 70 provides for selective activation of test wheel 26, and thus saves wear and tear on the test wheel and drive mechanism when the test wheel is initially lowered by winch 54 into engagement with the test surface. When clutch 70 is engaged, test wheel 26 is driven at predetermined slip, preferably thirteen percent slip, with respect to vehicle wheels 14. Power take-off 20 is also coupled by gear chain 60 through a second electric clutch 72 to pump 58. Clutch 72 thus provides for selective operator activation of the water pump so that water will not be wasted between test runs, and so that the vehicle-travelled surface can be tested for dry as well as wet friction characteristics. Pump 58 is connected to nozzle 64 through a flowmeter 74 for tracking the amount of water expended, and thereby advising the vehicle operator when water tank 62 is empty.

Test wheel 26 is coupled as previously described to the two-axis strain gage force transducer 30. Test wheel 26 is also coupled to a digital tachometer 76. Measurement electronics module 78 receives signals from transducer 30 indicative of horizontal and vertical forces on test wheel 26, and also receives a signal from tachometer 76 indicative of angular velocity of the test wheel. Electronics module 78, which is preferably positioned within the cabin of vehicle 12, determines frictional characteristics of the road surface, such as coefficient of friction or any other desired parameter, from the information obtained from tachometer 76 and transducer 30, and indicates such friction characteristics, as well as other suitable information, on an operator display 80.

Figure 5A:
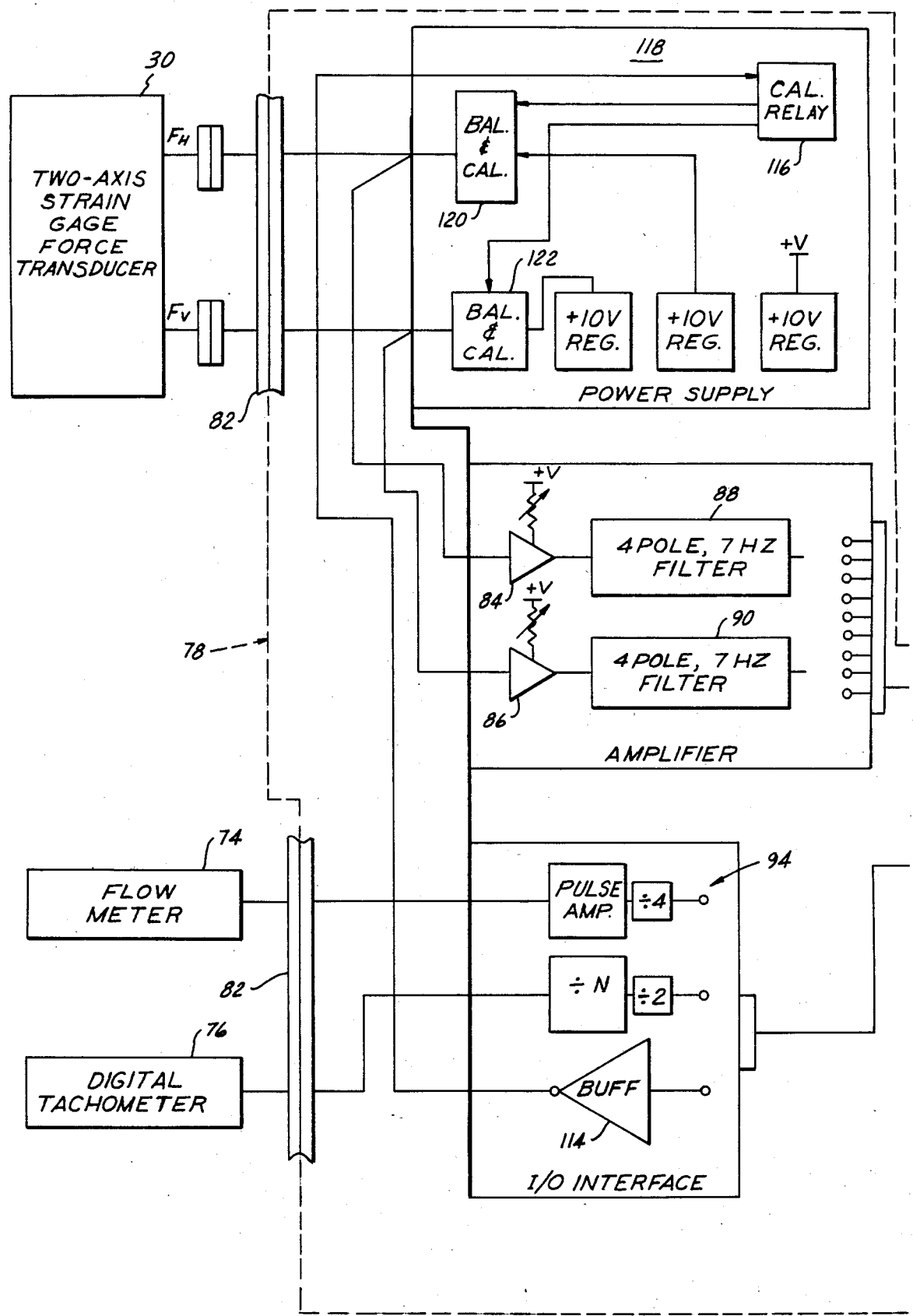

FIGS. 5A and 5B illustrate measurement electronics 78 in greater detail. The horizontal and vertical force-indicating outputs of transducer 30 are connected through a suitable connector 82 to inputs of respective amplifiers 84,86 (FIG. 5A). These input amplifiers are connected through respective four-pole lowpass filters 88,90 to the input port of an A/D converter 92 (FIG. 5B). Likewise, flowmeter 74 and digital tachometer 76 are connected through connector 82 (FIG. 5A) and through suitable amplification and division electronics 94 to the input/output port of an I/O interface 96 (FIG. 5B). A/D converter 92 and I/O interface 96 are connected by a digital bus 98 to a real time clock 100, a 64K RAM/EPROM 102 and a CPU 104. RAM/EPROM 102 includes suitable software for operating CPU 104 to input signals from transducer 30, flowmeter 74 and digital tachometer 76 through converter 92 and I/O interface 96 in the usual manner, and to compute therefrom frictional characteristics and other information desired to be measured. CPU 104 includes a suitable microprocessor and timer. A second I/O interface 106 is connected to bus 98, and through a graphic display interface 108 to operator display 80 for indicating measured parameters to the vehicle operator. CPU 104 has a first port connected to an operator keyboard 110 for inputting operator information directly into the CPU. A second port of CPU 104 is connected to a printer 112 for permanently recording measured friction characteristics and other suitable information.

I/O interface 96 (FIG. 5B) is also connected through a buffer 114 (FIG. 5A) to a calibration relay 116 in a power supply and calibration module 118. Module 118 provides regulated DC voltage to the remainder of measurement electronics 78, including a pair of calibration circuits 120,122. The outputs of calibration circuits 120,122, which may comprise suitable adjustable resistors, are connected to input amplifiers 84,86 for selectively calibrating amplifier gains. I/O interface 96 is also connected through an optical isolator 124 (FIG. 5B) to test wheel clutch 70 and water pump clutch 72, and to a relay 126 for driving electric winch 54 (FIG. 4). Operator pushbuttons 128 for controlling initiation and duration of a test cycle are connected to CPU 104 through isolator 124 and I/O interface 96.

The invention claimed is:

1. Apparatus for measuring a friction characteristic of a vehicle-travelled surface comprising: a wheeled vehicle constructed to be propelled in a predetermined direction along such a vehicle-travelled surface whose friction characteristic is to be measured; a test wheel assembly including a test wheel, hub means mounting said test wheel for rotation about a test wheel axis and transducer means coupled to said hub means for measuring forces on said test wheel at predetermined orientation to said wheel axis; drive means coupled to at least one wheel of said vehicle and to said test wheel for driving said test wheel at predetermined slip with respect to said at least one vehicle wheel; first suspension means mounting said drive means to said vehicle; second suspension means mounting said test wheel assembly to said vehicle for pivotal motion at an angle to said predetermined direction into and out of engagement with the travelled surface; and means responsive to said transducer means for indicating said friction characteristic;

characterized in that said first suspension means comprises means mounting said drive means to said vehicle against rotation of said drive means with respect to and about the drive axis of said drive means coupled to said at least one wheel, and in that said second suspension means comprises means for mounting said test wheel assembly including said transducer means to said drive means against rotation of said transducer means with respect to and about said test wheel axis so as to maintain said predetermined orientation of said transducer means to said wheel axis during pivotal motion of said wheel assembly.

2. The apparatus set forth in claim 1 wherein said first and second suspension means respectively comprise first and second parallelogram suspension means.

3. The apparatus set forth in claim 2 wherein said first parallelogram suspension means comprises a first pair of parallel strut means pivotally coupled at opposed ends to said vehicle and to said drive means.

4. The apparatus set forth in claim 3 wherein said second parallelogram suspension means comprises a second pair of parallel strut means pivotally coupled at opposed ends to said drive means and to said test wheel assembly.

5. The apparatus set forth in claim 4 wherein said vehicle comprises two wheels on a common axis; wherein said drive means comprises differential means coupled to said two vehicle wheels and endless gear drive means coupled from said differential means to said wheel assembly for driving said test wheel; and wherein said second pair of strut means comprises a housing enclosing said gear drive means and a control arm parallel to said housing.

6. The apparatus set forth in claim 5 wherein said vehicle comprises a self-propelled vehicle, said two vehicle wheels comprising rear wheels of said self-propelled vehicle.

7. The apparatus set forth in claim 6 wherein said hub means has a central hub axis; wherein said test wheel assembly further includes a test wheel drive shaft coupled to said drive means and mounted for rotation within said hub means; and wherein said transducer means includes a first portion mounted to said hub means for rotation about said hub axis, said control arm being pivotally coupled to said first portion, a second portion spaced from said hub and including means rotatably supporting said drive shaft within said second portion, and strain gage means rigidly coupled between said first and second portions for measuring said forces on said test wheel as a function of motion of said second portion with respect to said first portion.

8. The apparatus set forth in claim 7 wherein said drive means comprises an internally splined collar coupled to said gear drive means, and means forming crowned external splines on said shaft within said collar for maintaining a lever arm of substantially constant length from said drive means to said transducer means for tilting motion of said drive shaft with respect to said hub means.

9. The apparatus set forth in claim 8 wherein said transducer means comprises strain gage transducing means for separately measuring horizontal forces on said test wheel in said direction of travel, and vertical forces on said test wheel perpendicular to said direction of travel and to the travel surface.

10. The apparatus set forth in claim 7 further comprising an electric winch carried by said vehicle and coupled to said test wheel, and means responsive to a vehicle operator and coupled to said winch for selectively raising and lowering said test wheel with respect to the travel surface.

11. The apparatus set forth in claim 7 wherein said drive means further comprises first clutch means, and means connected to said first clutch means and responsive to a vehicle operator for selectively coupling said test wheel to said drive means.

12. The apparatus set forth in claim 11 further comprising means including a positive displacement pump carried by said vehicle and coupled to said differential means for directing a film of water of substantially uniform thickness independent of vehicle speed onto the travel surface beneath said test wheel.

13. The apparatus set forth in claim 12 wherein said pump-includind means comprises second clutch means, and means responsive to a vehicle operator and connected to said second clutch means for selectively coupling said pump to said differential means.

14. Apparatus for measuring a friction characteristic of a vehicle-travelled surface comprising:
a wheeled vehicle having at least two wheels on a common axis;
a test wheel assembly including a test wheel, hub means, a drive shaft rotatably carried at one end by said hub means and coupled at an opposing end to said test wheel for rotating said test wheel about a test wheel axis, a force transducer comprising a first portion coupled to said hub means for rotation about said test wheel axis, a second portion surrounding and rotatably supporting said drive shaft remotely of said one end and adjacent to said opposing end, and strain gage means rigidly coupled between said first and second portions;
drive means including differential means coupled to said two vehicle wheels, and gear drive means extending from said differential to said test wheel assembly for driving said shaft and said test wheel at predetermined velocity with respect to said vehicle wheels;
first parallel strut means suspending said differential from said vehicle against rotation about said common axis;
second parallel strut means suspending said test wheel assembly from said differential means against rotation of said first portion of said transducer about said test wheel axis; and
means responsive to said strain gage means for indicating said friction characteristic.

15. The apparatus set forth in claim 14 wherein said second parallel strut means comprises a housing enclosing said gear drive means and pivotally coupled at opposing ends to said differential means and said test wheel assembly, and a control arm parallel to said housing and pivotally coupled at opposing ends to said differential means and said first transducer portion.

16. The apparatus set forth in claim 15 wherein said drive means comprises an internally splined collar coupled to said gear drive means, and means forming crowned external splines on said shaft within said collar for maintaining a lever arm of substantially constant length from said drive means to said transducer means for tilting motion of said drive shaft with respect to said hub means.

* * * * *